US009456965B2

(12) United States Patent
Omura

(10) Patent No.: US 9,456,965 B2
(45) Date of Patent: Oct. 4, 2016

(54) OIL-IN-WATER EMULSIFIED SKIN COSMETIC

(71) Applicant: Shiseido Company, Ltd., Tokyo (JP)

(72) Inventor: Takayuki Omura, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 73 days.

(21) Appl. No.: 14/350,093

(22) PCT Filed: Nov. 22, 2012

(86) PCT No.: PCT/JP2012/080325
§ 371 (c)(1),
(2) Date: Apr. 7, 2014

(87) PCT Pub. No.: WO2013/103056
PCT Pub. Date: Jul. 11, 2013

(65) Prior Publication Data
US 2014/0343169 A1    Nov. 20, 2014

(30) Foreign Application Priority Data

Feb. 10, 2012  (JP) ................................ 2012-026995
Nov. 21, 2012  (JP) ................................ 2012-255445

(51) Int. Cl.
| | |
|---|---|
| A61K 8/06 | (2006.01) |
| A61K 8/73 | (2006.01) |
| A61Q 19/00 | (2006.01) |
| A61K 8/34 | (2006.01) |
| A61K 8/81 | (2006.01) |
| A61Q 19/02 | (2006.01) |
| A61Q 19/08 | (2006.01) |
| A61K 8/891 | (2006.01) |
| A61K 8/92 | (2006.01) |

(52) U.S. Cl.
CPC ............... *A61K 8/062* (2013.01); *A61K 8/345* (2013.01); *A61K 8/735* (2013.01); *A61K 8/8129* (2013.01); *A61K 8/8152* (2013.01); *A61K 8/8158* (2013.01); *A61K 8/891* (2013.01); *A61K 8/92* (2013.01); *A61K 8/922* (2013.01); *A61Q 19/00* (2013.01); *A61Q 19/02* (2013.01); *A61Q 19/08* (2013.01)

(58) Field of Classification Search
None
See application file for complete search history.

(56) References Cited

U.S. PATENT DOCUMENTS 5,679,657 A * 10/1997 Oka et al. ........................ 514/54
6,335,037 B1 * 1/2002 Ichinohe .................. A61K 8/25
424/401

| | | | | |
|---|---|---|---|---|
| 2001/0055580 A1 * | 12/2001 | Belli et al. | .................. | 424/70.16 |
| 2007/0154439 A1 * | 7/2007 | Dorf | .......................... | 424/70.31 |
| 2009/0104129 A1 * | 4/2009 | Chen | .................... | A61K 8/4973 |
| | | | | 424/59 |
| 2009/0202600 A1 | 8/2009 | Omura | | |
| 2009/0269374 A1 * | 10/2009 | Lee et al. | ...................... | 424/401 |
| 2010/0292509 A1 | 11/2010 | Kajiya | | |
| 2013/0079368 A1 | 3/2013 | Omura | | |

FOREIGN PATENT DOCUMENTS

| | | |
|---|---|---|
| EP | 0 725 083 A1 | 8/1996 |
| JP | 2000-219619 A | 8/2000 |
| JP | 2005-068073 A | 3/2005 |
| JP | 2005-272389 A | 10/2005 |
| JP | 2006-022047 A | 1/2006 |
| JP | 2011-020966 A | 2/2011 |
| WO | 96/05233 A1 | 2/1996 |
| WO | 2009/093534 A1 | 7/2009 |
| WO | 2011/158679 A1 | 12/2011 |

OTHER PUBLICATIONS

JP 2005-068073, Machine Translatoin, retrieved online on Mar. 24, 2015.*
Sigma-Aldrich, Glyceryl trioctanoate—Safety Data Sheet, Jun. 10, 2015, p. 1-6.*
Machine Translation of JP2011-020966, 2011, p. 1-37.*
Machine Translation of JP2005-068073, 2005, p. 1-17.*
The International Bureau of WIPO, "Notification of Transmittal of Translation of the International Preliminary Report on Patentability," issued in International Application No. PCT/JP2012/080325, of which U.S. Appl. No. 14/350,093 is a U.S. national phase entry, with a date of mailing of Aug. 21, 2014.
Shiseido Co., Ltd, Shiseido Sodium Hyaluronate: Sodium Acetyl Hyaluronate (Cosmetic Grade: Derivative), [online] <http://ha.shiseido.co.jp/e/cosmetic/derivative.htm>, retrieved May 14, 2015.
European Patent Office, "Extended European Search Report," issued in European Patent Application No. 12 358 689.8, which is a European counterpart of U.S. Appl. No. 14/350,093, with an issuance date of Dec. 4, 2015, 8 pages.

* cited by examiner

*Primary Examiner* — Jennifer Berrios

(57) ABSTRACT

The present invention is an oil-in-water emulsified skin cosmetic comprising acetylated hyaluronic acid, a specific polymethacryloyloxyethyl phosphorylcholine derivative, non-emulsifying cross-linked silicone, glycerin, polyvinyl alcohol, an acrylamide type thickener, and an oil component in an amount of 25 wt % or more relative to the total amount of the oil-in-water emulsified skin cosmetic.

The object of the present invention is to provide an oil-in-water emulsified skin cosmetic manifesting superior effects in improving spreadability on the skin, absorption in the skin, absence of stickiness, emollient sensations, taut sensations, and wrinkles/sagging.

7 Claims, 1 Drawing Sheet

OIL-IN-WATER EMULSIFIED SKIN COSMETIC

CROSS REFERENCE TO RELATED APPLICATIONS

This patent application is a U.S. national stage application under 35 U.S.C. §371 of International Patent Application No. PCT/JP2012/080325 filed on Nov. 22, 2012, which claims the benefit of foreign priority to Japanese Patent Application No. JP 2012-026995 filed on Feb. 10, 2012, and to Japanese Patent Application No. JP 2012-255445 filed on Nov. 21, 2012, the disclosures of all of which are hereby incorporated by reference in their entireties. The International Application was published in Japanese on Jul. 11, 2013, as International Publication No. WO 2013/103056 A1 under PCT Article 21(2).

TECHNICAL FIELD

The present invention relates to an oil-in-water emulsified skin cosmetic. More specifically, it relates to an oil-in-water emulsified skin cosmetic manifesting superior effects in improving spreadability on the skin, absorption into the skin, absence of stickiness, emollient sensations, taut sensations, and wrinkles/sagging.

BACKGROUND ART

Conventionally, oil-in-water emulsified skin cosmetics have been prepared by emulsifying solid oils including polyhydric alcohols such as glycerin, 1,3-butylene glycol, and dipropylene glycol, higher fatty acids such as stearic acid, palmitic acid, myristic acid, and behenic acid, waxes such as petrolatum, carnauba wax, candelilla wax, ceresin, and microcrystalline wax, and higher alcohols such as lauryl alcohol, myristyl alcohol, palmityl alcohol, stearyl alcohol, and behenyl alcohol in order to enhance moist-rich sensations, smooth spreadability, and emollient sensations. In order to suppress crystal precipitation of these solid oils over time, attempts have been made to avoid crystal precipitation of the solid oils by adding hydrocarbon oils that are compatible with said solid oils and are liquid at ordinary temperatures such as liquid paraffin and squalane and ester oils having relatively long carbon chains, equivalent in length to the carbon chains of the solid oils, such as cetyl palmitate, isopropyl isostearate, isodecyl pivalate, and oleyl oleate (for example, refer to Non-Patent Document 1).

However, oil-in-water emulsified skin cosmetics prepared by emulsifying solid oils with the method as described above, when applied on the skin, manifest emollient sensations and taut sensations but the effects do not last more than a half day, or 12 hours, spreadability and absorption into the skin is not good, and they are sticky, resulting in unsatisfactory usability.

On the other hand, when solid oils are not added, the products are superior in that spreadability and absorption into the skin are good and there is no stickiness, but an absence of the emollient sensation and taut sensation becomes problematic.

Patent Document 1 discloses a cosmetic for the eye area comprising acetylated hyaluronic acid, corresponding to ingredient (A) in the present invention, a polymethacryloyloxyethyl phosphorylcholine derivative, corresponding to ingredient (B) in the present invention, and polyhydric alcohol, corresponding to ingredient (D), glycerin, in the present invention.

However, although this cosmetic gives an emollient sensation right after application, it has a problem in that it doesn't give a sense of an improvement in the tautness right after the application and an improvement in wrinkles/sagging right after the application.

PRIOR ART DOCUMENTS

Patent Documents

Patent Document 1: JP 2005-68073 A

Non-Patent Documents

Non-Patent Document 1: "Saishin-Keshohin-Kagaku [Newest Cosmetic Science](revised and enlarged 11)", Yakuji Nippo Limited, Jul. 10, 1992, pp. 49, Edited by The Society of Cosmetic Chemists of Japan

OUTLINE OF THE INVENTION

Problem that the Present Invention Aims to Solve

The present invention was completed in view of the aforementioned problems and its object is to provide an oil-in-water emulsified skin cosmetic manifesting superior effects in improving spreadability on the skin, absorption into the skin, absence of stickiness, emollient sensations, taut sensations, and wrinkles/sagging by using acetylated hyaluronic acid and a polymethacryloyloxyethyl phosphorylcholine derivative.

Means to Solve the Problem

That is, the present invention provides an oil-in-water emulsified skin cosmetic comprising the following ingredients (A) through (G):

(A) Acetylated hyaluronic acid represented by the following structural formula (I):

{Chemical formula 1}

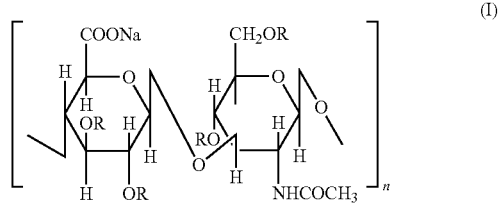

(R denotes H or $COCH_3$. n is a real number representing the degree of polymerization.)

(B) A polymethacryloyloxyethyl phosphorylcholine derivative having the following structural formula (II):

{Chemical formula 2}

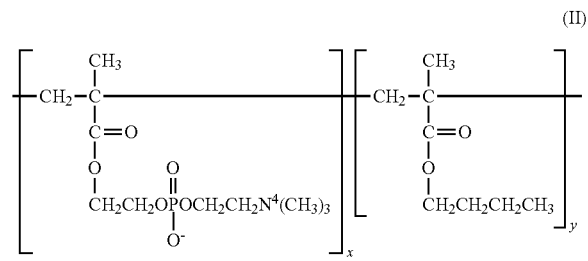

(x and y are real numbers representing the degrees of polymerization of the corresponding structural units: x/y=2/8 to 8/2.)
(C) One, two or more types of non-emulsifying cross-linked silicone
(D) Glycerin
(E) Polyvinyl alcohol
(F) Acrylamide-type thickener
(G) Oil component in a total amount of 25 wt % or more relative to the total amount of the oil-in-water emulsified skin cosmetic Also, the present invention provides the aforementioned oil-in-water emulsified skin cosmetic wherein the aforementioned ingredient (A), acetylated hyaluronic acid, has 2.6-3.8 of the four alcoholic hydroxy groups in the repeating unit of acetylated hyaluronic acid represented by the following structural formula (I) replaced by acetyl groups and the limiting viscosity is 50-200 cm$^3$/g.

{Chemical formula 3}

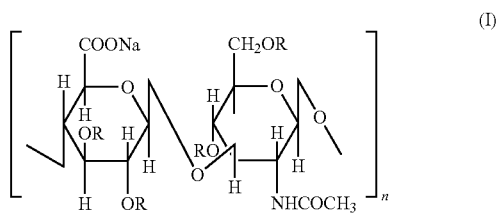

(R denotes H or $COCH_3$. n is a real number representing the degree of polymerization.)

Furthermore, the present invention provides the aforementioned oil-in-water emulsified skin cosmetic wherein the blend ratio of the aforementioned ingredient (A), acetylated hyaluronic acid, is 0.001-0.1 wt %, the blend ratio of the aforementioned ingredient (B), the polymethacryloyloxyethyl phosphorylcholine derivative, is 0.003-0.3 wt %, the blend ratio of ingredient (C), one, two or more types of non-emulsifying type cross-linked silicone, is 0.5-5.0 wt %, the blend ratio of ingredient (D), glycerin, is 5.0-10.0 wt %, the blend ratio of ingredient (E), polyvinyl alcohol, is 0.1-1.0 wt %, the blend ratio of ingredient (F), the acrylamide type thickener, is 0.1-1.0 wt %, and the blend ratio of ingredient (G), the oil component, is 25-40 wt %.

Also, the present invention provides the aforementioned oil-in-water emulsified skin cosmetic wherein the weight-average molecular weight of the said ingredient (B), polymethacryloyloxyethyl phosphorylcholine derivative, is 100,000 to 1,000,000.

Furthermore, the present invention provides the aforementioned oil-in-water emulsified skin cosmetic wherein said ingredient (C), non-emulsifying cross-linked silicone, is one, two or more selected from a group consisting of dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and (dimethicone/bis-isobutyl PPG-20) crosspolymer.

Also, the present invention provides the aforementioned oil-in-water emulsified skin cosmetic wherein said (F) acrylamide-type thickener is vinylpyrrolidone/2-acrylamide-2-methylpropane sulfonic acid copolymer and/or sodium N,N'-dimethylacrylamide-2-acrylamide-2-methlylpropane sulfonate/N,N'-methylenebisacrylamide copolymer.

Effects of the Invention

The oil-in-water emulsified skin cosmetic of the present invention manifests superior effects in improving spreadability on the skin, absorption into the skin, absence of stickiness, emollient sensations, taut sensations, and wrinkles/sagging.

It is particularly superior in terms of the moisture-retention effect and therefore the present invention characteristically manifests superior sustention of the emollient sensation.

THE EMBODIMENTS OF THE PRESENT INVENTION

Figure 1:
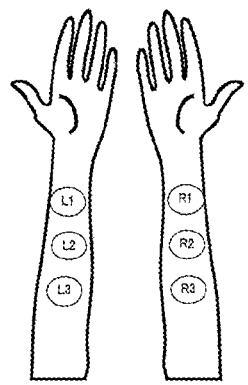
FIG. 1 is an illustration of a forearm that shows the application site of the sample of Examples.

The present invention is described in detail below.
"(A) Acetylated Hyaluronic Acid Having Structural Formula (I)"
The acetylated hyaluronic acid used in the present invention is an acetylated hyaluronic acid having the following structural formula (I):

{Chemical formula 4}

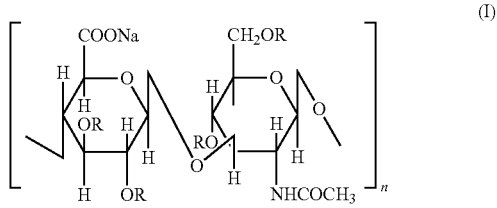

(R denotes H or $COCH_3$. n is a real number representing the degree of polymerization.)

The acetylated hyaluronic acid used in the present invention should preferably have a low molecular weight. Since it is difficult to directly specify the molecular weight of the acetylated hyaluronic acid, in the present invention the measurement of the limiting viscosity in a 0.2 M phosphate buffer (pH=7.3) at 25° C. is used to specify "low molecular weight." "Low molecular weight" of the low molecular weight acetylated hyaluronic acid preferable for the present invention is required to be 50-200 cm³/g in terms of the limiting viscosity.

If the limiting viscosity is less than 50 cm³/g, the emollient sensation from the acetylated hyaluronic acid may be hard to obtain. If it is higher than 200 cm³/g, then it may not be possible to sufficiently suppress undesirable physical properties such as a thread-forming property even by acetylation.

The acetylated hyaluronic acid used in the present invention preferably has an acetyl group substitution number of 2.6 or more and 3.8 or less.

Acetylated hyaluronic acid, as shown in the aforementioned structural formula (I), has four alcoholic hydroxy groups in a repeating unit, and the acetyl group substitution number is defined as the average number of them replaced by acetyl groups.

If the number of acetyl group substitutions is less than 2.6, then the endowed hydrophobicity tends to be insufficient. If it is more than 3.6, then a reduction in hydrophilicity, worsening of usability, etc. may occur.

JP H06-9707 A discloses highly acetylated hyaluronic acid; however, it is rather directed toward high molecular weight acetylated hyaluronic acid, which is different from the low molecular weight acetylated hyaluronic acid preferably used in the present invention. For the low molecular weight acetylated hyaluronic acid preferably used in the present invention, low molecular weight acetylated hyaluronic acid prepared according to the preparation method disclosed in JP H9-71062 A is used.

The blend ratio of ingredient (A), acetylated hyaluronic acid, is preferably 0.001-0.1 wt % relative to the total amount of the oil-in-water emulsified skin cosmetic. If the blend ratio is less than 0.001 wt %, then the sustained emollient sensation, which is an effect of the present invention, becomes inferior; on the other hand, if the blend ratio exceeds 0.1 wt %, then a problem may arise in terms of absorption into the skin and stickiness.

"(B) A Polymethacryloyloxyethyl Phosphorylcholine Derivative Having Structural Formula (II)"

Ingredient (B) used in the present invention is represented by the following structural formula (II) and it is a prior art polymethacryloyloxyethyl phosphorylcholine derivative disclosed in JP H7-10892 A. In the present invention, a commercial product (Lipidure-PMB from NOF corporation) can be used.

{Chemical formula 5}

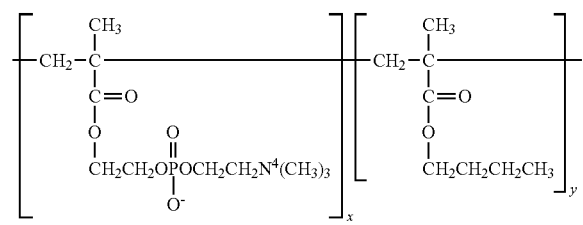

(II)

(x and y are real numbers representing the degrees of polymerization of the corresponding structural units: x/y=2/8 to 8/2.)

In the structural formula, x and y denote the degrees of polymerization of the corresponding structural units; x/y is preferably 2/8 to 8/2. The reason for this is as follows: if x/y is less than 2/8, then the sustained emollient sensation, which is an effect of the present invention, becomes inferior; on the other hand, if x/y exceeds 8/2, then the oil-in-water emulsified skin cosmetic of the present invention becomes sticky.

Also, the weight average molecular weight of said ingredient (B), polymethacryloyloxyethyl phosphorylcholine derivative, is preferably 100,000-1,000,000, more preferably 600,000-700,000.

In the present invention, weight average molecular weight stands for the polystyrene equivalent value measured with GPC.

The blend ratio of ingredient (B), polymethacryloyloxyethyl phosphorylcholine, is preferably 0.003-0.3 wt % relative to the total amount of the oil-in-water emulsified skin cosmetic. The reason for this is as follows: if it is less than 0.003 wt %, then the sustained emollient sensation, which is an effect of the present invention, becomes inferior; on the other hand, if it exceeds 0.3 wt %, then the oil-in-water emulsified skin cosmetic of the present invention may become sticky.

"(C) One, Two or More Types of Non-Emulsifying Cross-Linked Silicone"

The non-emulsifying type cross-linked silicone used in the present invention is a cross-linked silicone in which some of the silicone chains are cross-linked, characterized by not having its own ability to emulsify oil and water. A cross-linked silicone is verified as non-emulsifying when a composition having water, oil, and the cross-linked silicone is stirred at a high speed using a homomixer and as a result emulsification does not occur or emulsification occurs but the particle size of the emulsified particles is large, 50 μm or more, and the emulsified state does not last when allowed to stand for a while.

Ingredient (C), non-emulsifying cross-linked silicone, is preferably one, two or more selected from a group consisting of dimethicone crosspolymer, (dimethicone/vinyl dimethicone) crosspolymer, (dimethicone/phenyl vinyl dimethicone) crosspolymer, (vinyl dimethicone/lauryl dimethicone) crosspolymer, (lauryl polydimethylsiloxyethyl dimethicone) crosspolymer, alkyl (C30-45) cetearyl dimethicone crosspolymer, cetearyl dimethicone crosspolymer, and (dimethicone/bis-isobutyl PPG-20) crosspolymer.

The (dimethicone/vinyl dimethicone) crosspolymer is sometimes also called polysilicone-11.

The blend ratio of the non-emulsifying cross-linked silicone is preferably 0.1-5.0 wt % relative to the total amount of the oil-in-water emulsified skin cosmetic. If the blend ratio is less than 0.1 wt % then the effect of the present invention is hard to obtain; on the other hand, adding more than 5.0 wt % would not increase the effect and stickiness may result.

When preparing the oil-in-water emulsified skin cosmetic of the present invention, it is preferable to blend in the aforementioned non-emulsifying cross-linked silicone in a swollen form (gel composition) swollen with a liquid oil component. This way, an oil-in-water emulsified skin cosmetic having a superior effect can be prepared in a stable form.

For the liquid oil component for this, a liquid oil component having a low viscosity at ordinary temperatures, 100 mPa·s or less for example, is preferable. A preferable viscosity range is 1-100 mPa·s; cyclomethicone, methyl trimethicone, etc. can be used, for example.

In the non-emulsifying cross-linked silicone swollen with the liquid oil, which is a preferable form for blending, a preferable mass ratio of the non-emulsifying cross-linked silicone to the liquid oil is 5-40 to 95-60. In this mass ratio range, a preferable swollen form for blending the non-emulsifying cross-linked silicone into the oil-in-water emulsified skin cosmetic of the present invention is obtained.

The aforementioned swollen form of the non-emulsifying cross-linked silicone is commercially available and therefore such commercial products can be used, examples of which follow.

(1) Examples of a swollen form having the designation "dimethicone crosspolymer" include DC9040 (a mixture of dimethicone crosspolymer and decamethylcyclopentasiloxane, approximately 12% of which is cross-linked), DC9041 (a mixture of dimethicone crosspolymer and dimethicone 5 mPa·s, approximately 16% of which is cross-linked), and DC9045 (a mixture of dimethicone crosspolymer and decamethylcyclopentasiloxane, approximately 12.5% of which is cross-linked), all of which are from Dow Corning Toray.

(2) Examples of a swollen form having the designation "(dimethicone/vinyldimethicone) crosspolymer, or polysilicone-11, include KSG-15 (a mixture of (dimethicone/vinyl dimethicone) crosspolymer and cyclopentasiloxane, approximately 5% of which is cross-linked), KSG-16 (a mixture of (dimethicone/vinyl dimethicone) crosspolymer and dimethicone 6 mPa·s, approximately 25% of which is cross-linked), KSG-1610 (a mixture of (dimethicone/vinyldimethicone) crosspolymer and methyl trimethicone, approximately 17.5% of which is cross-linked) (these are from Shin-Etsu Chemical Co., Ltd.), GRANSIL GCM (a mixture of polysilicone-11 and octamethylcyclotetrasiloxane, approximately 6% of which is cross-linked), GRANSIL GCM-5 (a mixture of polysilicone-11 and decamethylcyclopentasiloxane, approximately 6% of which is cross-linked), GRANSIL IDS (a mixture of polysilicone-11 and isodecane, approximately 7% of which is cross-linked), GRANSIL DMG-6 (a mixture of polysilicone-11 and dimethicone 6 mPa·s, approximately 18% of which is cross-linked), GRANSIL DMG-20 (a mixture of polysilicone-11 and dimethicone 20 mPa·s, approximately 25% of which is cross-linked), GRANSIL DMG-50 (a mixture of polysilicone-11 and dimethicone 50 mPa·s, approximately 26% of which is cross-linked), and GRANSIL PM (a mixture of polysilicone-11 and phenyl trimethicone, approximately 20% of which is cross-linked), and GRANSIL ININ (a mixture of polysilicone-11 and isononyl isononanoate, approximately 15% of which is cross-linked) (these are from GRANT Inc.).

(3) Examples of a swollen form having the designation "(dimethicone/phenyl vinyl dimethicone) crosspolymer" include KSG-18 (a mixture of (dimethicone/vinyl dimethicone) crosspolymer and phenyl trimethicone, approximately 15% of which is cross-linked) (from Shin-Etsu Chemical Co., Ltd.).

(4) Examples of a swollen form having the designation "(vinyl dimethicone/lauryl dimethicone) crosspolymer" include KSG-41 (a mixture of (vinyl dimethicone/lauryl dimethicone) crosspolymer and liquid petrolatum, approximately 30% of which is cross-linked), KSG-42 (a mixture of (vinyl dimethicone/lauryl dimethicone) crosspolymer and light isoparaffin, approximately 25% of which is cross-linked), KSG-43 (a mixture of (vinyl dimethicone/lauryl dimethicone) crosspolymer and glyceryl tri-2-ethylhexanoate, approximately 30% of which is cross-linked), and KSG-44 (a mixture of (vinyl dimethicone/lauryl dimethicone) crosspolymer and squalane, approximately 5% of which is cross-linked), all of which are from Shin-Etsu Chemical Co., Ltd.

(5) Examples of a swollen form having the designation "(lauryl polydimethylsiloxyethyl dimethicone/bis-vinyl dimethicone) crosspolymer" include KSG-042Z (a mixture of (lauryl polydimethylsiloxyethyl dimethicone/bis-vinyl dimethicone) crosspolymer and isododecane, approximately 20% of which is cross-linked) and KSG-045Z (a mixture of (lauryl polydimethylsiloxyethyl dimethicone/bis-vinyl dimethicone) crosspolymer and cyclopentasiloxane, approximately 20% of which is cross-linked), all of which are from Shin-Etsu Chemical Co., Ltd.

(6) Examples of a swollen form having the designation "alkyl (C30-45) cetearyl dimethicone crosspolymer" include VELVESIL 125 (a mixture of alkyl (C30-45) cetearyl dimethicone crosspolymer and cyclopentasiloxane, approximately 12.5% of which is cross-linked) and VELVESIL 034 (a mixture of alkyl (C30-45) cetearyl dimethicone crosspolymer and caprylyl methicone, approximately 16% of which is cross-linked), which are from Momentive Performance Materials Japan LLC.

(7) Examples of a swollen form having the designation "cetearyl dimethicone crosspolymer" include VELVESIL DM (a mixture of cetearyl dimethicone crosspolymer and dimethicone, approximately 17% of which is cross-linked, which is from Momentive Performance Materials Japan LLC.

(8) Examples of a swollen form having the designation "(dimethicone/bis-isobutyl PPG-20) crosspolymer" include EL-8050ID Silicone Organic Elastomer Blend (a mixture of (dimethicone/isobutyl PPG-20) crosspolymer and isododecane, approximately 15% of which is cross-linked) and EL-8050ID Silicone Organic Elastomer Blend (a mixture of (dimethicone/isobutyl PPG-20) crosspolymer and isodecyl neopentanoate, approximately 12% of which is cross-linked).

In the present invention, said swollen form is used in such a way that the weight percentage of the non-emulsifying cross-linked silicone is 0.5-5.0 wt % relative to the total amount of the oil-in-water emulsified skin cosmetic. If it is less than 0.5 wt %, then the effects of the present invention cannot be obtained. On the other hand, if the blend ratio exceeds 5.0 wt %, then stickiness arises.

"(D) Glycerin"

For ingredient (D), glycerin, for use in the present invention, those normally used for skin cosmetics can be used. The blend ratio is preferably 5.0-10.0 wt % relative to the total amount of the oil-in-water emulsified skin cosmetic.

"(E) Polyvinyl Alcohol"

For ingredient (E), polyvinyl alcohol, for use in the present invention, those normally used for skin cosmetics can be used. The blend ratio is preferably 0.1-1.0 wt % relative to the total amount of the oil-in-water emulsified skin cosmetic.

"(F) Acrylamide-Type Thickener"

Ingredient (F), acrylamide-type thickener, is preferably vinylpyrrolidone/2-acrylamide-2-methylpropane sulfonic acid copolymer and/or sodium N,N'-dimethylacrylamide-2-acrylamide-2-methlylpropane sulfonate/N,N'-methylenebisacrylamide copolymer.

If thickeners other than acrylamide-type thickeners (xanthan gum, for example) are used, the effects of the present invention are not sufficiently manifested (refer to Example 3 and Comparative example 4). From this point of view as well, the configuration of the present application is not an invention that a person skilled in the art can easily come up with.

The blend ratio of (F) acrylamide-type thickener is preferably 0.1-1.0 wt % relative to the total weight of the oil-in-water emulsified skin cosmetic.

In addition to the aforementioned essential ingredients, surfactants (emulsifiers), oil components, and water necessary to prepare the oil-in-water emulsified skin cosmetic are added to the oil-in-water emulsified skin cosmetic of the present invention. Details are described below.

"Surfactant (Emulsifier)"

Depending on the product, any surfactant is blended in.

Examples include anionic surfactants including soap materials, fatty acid soaps such as sodium laurate and sodium palmitate, higher alkyl sulfates such as sodium lauryl sulfate and potassium lauryl sulfate, alkyl ether sulfates such as triethanolamine POE lauryl sulfate and sodium POE lauryl sulfate, N-acyl sarcosinates such as sodium lauroyl sarcosinate, higher fatty acid amide sulfonic acids such as sodium N-myristoyl-N-methyltaurate and sodium cocoyl methyltaurate, phosphoric esters such as POE stearyl ether phosphate, sulfosuccinates such as sodium mono lauroyl monoethanolamide POE sulfosuccinates and sodium lauryl polypropylene glycol sulfosuccinates, alkyl benzene sulfonates such as sodium linear dodecyl benzene sulfonate and triethanolamine linear dodecyl benzene sulfonate, N-acyl glutamates such as disodium N-stearoyl glutamate and monosodium N-stearoyl glutamate, higher fatty acid ester sulfates such as hydrogenated coconut oil aliphatic acid glycerin sodium sulfate, sulfated oils such as turkey red oil, POE alkyl ether carboxylic acid, POE alkyl allyl ether carboxylate, higher fatty acid ester sulfonate, sec-alcohol sulfate, higher fatty acid alkylol amide sulfate, sodium lauroyl monoethanolamide succinate, and sodium caseinate; cationic surfactants including alkyl trimethyl ammonium salts such as stearyl trimethyl ammonium chloride and lauryl trimethyl ammonium chloride, dialkyl dimethyl ammonium salts such as distearyl dimethyl ammonium chloride, alkyl pyridinium salts such as cetyl pyridinium chloride, alkyl quaternary ammonium salt, alkyl dimethyl benzyl ammonium salt, alkyl isoquinolinium salt, dialkyl morphonium salt, POE alkyl amine, alkyl amine salt, polyamine fatty acid derivatives, amyl alcohol fatty acid derivatives, and benzalkonium chloride; ampholytic surfactants including imidazoline-type ampholytic surfactants such as 2-cocoyl-2-imidazolinium hydroxide-1-carboxyethyloxy disodium salt, amido betaine, and sulfobetaine; lipophilic nonionic surfactant including sorbitan fatty acid esters such as sorbitan monooleate, sorbitan monoisostearate, sorbitan monolaurate, sorbitan monopalmitate, and sorbitan trioleate, glycerin polyglycerin fatty acids such as mono cottonseed oil fatty acid glycerin, glycerin monostearate, glycerin sesquioleate, and glycerin monostearate malate, propylene glycol fatty acid esters such as propylene glycol monostearate, hydrogenated caster oil derivatives, glycerin alkyl ether, and POE/methylpolysiloxane copolymer; and hydrophilic nonionic surfactants such as POE sorbitan fatty acid esters such as POE sorbitan monooleate and POE sorbitan monostearate, POE sorbitol fatty esters such as POE sorbitol monolaurate, POE sorbitol monooleate, and POE sorbitol monostearate, POE glycerin fatty acid esters such as POE glycerin monooleate and POE glycerin distearate, POE fatty acid esters such as POE monooleate, POE distearate, and POE dioleate, POE alkyl ethers such as POE lauryl ether, POE oleyl ether, and POE cholestenol ester, POE alkyl phenyl ethers such as POE octyl phenyl ether and POE nonyl phenyl ether, POE/POP alkyl ethers such as POE/polyoxypropylene (hereafter referred to as POP) monobutyl ether, POE/POP cetyl ether, POE/POP glycerin ether, POE caster oil hydrogenated caster oil derivatives such as POE caster oil, POE hydrogenated caster oil, POE caster oil monoisostearate, and POE hydrogenated caster oil maleic acid, POE beeswax/lanolin derivatives such as POE sorbitol beeswax, alkanol amides such as palm oil fatty acid diethanol amide such as fatty acid isopropanol amide, POE propylene glycol fatty acid ester, POE fatty acid amide, POE alkylamine, sucrose fatty acid ester, and alkyl ethoxy dimethyl amine oxide.

Surfactants that are particularly preferable for the present invention include nonionic surfactants such as POE alkyl ethers and POE fatty acid esters.

The blend ratio of the surfactant is appropriately determined based on the type; preferably it is 0.5-3.0 wt % relative to the total amount of the oil-in-water emulsified skin cosmetic.

"(G) Oil Component(s) in the Total Amount of 25 wt % or More Relative to the Total Amount of the Oil-in-Water Emulsified Skin Cosmetic"

Depending on the product, any oil component is blended in. Examples include liquid fats and oils such as avocado oil, tsubaki oil, turtle fatty acid, macadamia nut oil, corn oil, mink oil, olive oil, rapeseed oil, egg yolk oil, sesame oil, persic oil, wheat germ oil, sasanqua oil, castor oil, linseed oil, safflower oil, cotton seed oil, evening primrose oil, perilla oil, soybean oil, peanut oil, tea seed oil, Japanese nutmeg oil, rice bran oil, Chinese gimlet oil, Japanese gimlet oil, jojoba oil, germ oil, and triglycerin, glycerin trioctanoate, and glycerin triisopalmitate;

solid fats and oils such as cacao butter, coconut oil, horse fat, hydrogenated coconut oil, palm oil, beef tallow, mutton tallow, hydrogenated beef tallow, palm kernel oil, lard, Japanese core wax nucleus oil, hydrogenated oil, Japanese core wax, and hydrogenated castor oil;

waxes such as beeswax, candelilla wax, cotton wax, carnauba wax, lanolin, lanolin acetate, liquid lanolin, sugar cane wax, lanolin fatty acid isopropyl ester, hexyl laurate, reduced lanolin, jojoba wax, hard lanolin, polyoxyethylene (hereafter referred to as POE) lanolin alcohol ether, POE lanolin alcohol acetate, lanolin fatty acid polyethylene glycol, and POE hydrogenated lanolin ethyl alcohol ether;

hydrocarbon oils such as liquid petrolatum, ozocerite, squalene, paraffin, ceresin, squalane, petrolatum, and microcrystalline wax;

and ester oils such as isopropyl myristate, cetyl octanoate, octyl dodecyl myristate, isopropyl palmitate, butyl stearate, hexyl laurate, myristyl myristate, decyl oleate, hexyl decyl dimethyloctanoate, cetyl lactate, myristyl lactate, lanolin acetate, isocetyl stearate, isocetyl isostearate, cholesteryl 12-hydroxystearate, ethylene glycol di(2-ethylhexanoate), dipentaerythritol fatty acid ester, n-alkylene glycol monoisostearate, neopentyl glycol dicaprate, diisostearyl malate, glyceryl di-2-heptylundecanoate, trimethylolpropane tri-2-ethylhexylate, trimethylolpropane triisostearate, pentaerythritol tetra-2-ethylhexylate, glycerin tri-2-ethylhexylate, trimethylolpropane triisostearate, cetyl 2-ethyl hexanoate, 2-ethylhexyl palmitate, glycerin trimyristate, tri-2-heptyl undecanoic acid glyceride, castor oil fatty acid methyl ester, oleyl oleate, acetoglyceride, 2-heptylundecyl palmitate, diisopropyl adipate, 2-octyldodecyl N-lauroyl-L-glutamate, di-2-heptylundecyl adipate, di-2-ethylhexyl sebacate, 2-hexyldecyl myristate, 2-hexyldecyl palmitate, 2-hexyldecyl adipate, diisopropyl sebacate, and 2-ethylhexyl succinate; higher fatty acids such as lauric acid, myristic acid, palmitic acid, stearic acid, behenic acid, oleic acid, 12-hydroxystearic acid, undecylenic acid, isostearic acid, linolic acid, linoleic acid, and eicosapentanoeic acid; straight-chain or branched-chain alcohols such as lauryl alcohol, cetyl alcohol, stearyl alcohol, behenyl alcohol, myristyl alcohol, oleyl alcohol, cetostearyl alcohol, mono stearyl glycerin ether (batyl alcohol), 2-decyltetradecynol, lanolin alcohol, cholesterol, phytosterol, hexyl dodecanol, isostearyl alcohol, and octyl dodecanol;

silicone oils such as dimethylpolysiloxane and methyl phenyl polysiloxane;

and perfluoropolyethers or perfluorocarbons such as perfluorohexane and tri-perfluoro-n-butyl amine.

Examples of oil components particularly preferable for the present invention include higher alcohols, ester oils, and silicone oils.

The type and the blend ratio of the oil component is appropriately determined based on the type of the product, i.e., emulsion, cream, etc.; the total blend ratio is 25.0 wt % or more relative to the total amount of the oil-in-water emulsified skin cosmetic. It is preferably 25.0-40.0 wt % relative to the total amount of the oil-in-water emulsified skin cosmetic.

If the total amount of the oil component is 25 wt % or more, then superior effects are manifested in improving emollient sensations, taut sensations, and wrinkles/sagging; if it is less than 25 wt %, then these effects are not manifested sufficiently (refer to Example 1 in Table 1 and the effect of less than 25 wt % of ingredient (G) oil component).

"Water"

For water, preferably used are ion-exchanged water and purified water. The blend ratio is appropriately determined based on the type of the product; preferably it is 40.0-80.0 wt % relative to the total amount of the oil-in-water emulsified skin cosmetic.

In addition to the aforementioned essential ingredients, other ingredients normally used in external preparations such as cosmetics and drugs can be blended in as necessary in the oil-in-water emulsified skin cosmetic of the present invention; examples of such ingredients include powders, coloring agents, alcohols, chelating agents, silicones, antioxidants, ultraviolet absorbents, humectants, perfumes, various medicinal ingredients, preservatives, neutralizing agents, and pH adjustment agents; and the oil-in-water emulsified skin cosmetic can be prepared with a conventional method. Specific optional ingredients are listed below; these ingredients can be combined appropriately and blended in according to the formulation for a desired product form.

Examples of the powders include mica, talc, kaolin, sericite, muscovite, phlogopite, synthetic mica, lepidolite, biotite, lithia mica, synthetic mica, calcium carbonate, magnesium carbonate, silicic acid anhydride, aluminum silicate, barium silicate, calcium silicate, magnesium silicate, strontium silicate, aluminum oxide, barium sulfate, red iron oxide, yellow iron oxide, black iron oxide, cobalt oxide, ultramarine blue, indigo blue, titanium oxide, zinc oxide, titanium mica (titanium oxide-coated mica), argentine, bithmus oxychloride, boron nitride, red 228, red 226, blue 404, polyethylene powder, methyl polymethacrylate powder, polyamide resin powder (nylon powder), cellulose powder, organopolysiloxane elastomer, aluminum powder, and copper powder.

Examples of the alcohols include lower alcohols such as ethanol, propanol, and isopropanol; and cholesterol, sitosterol, and lanosterol.

Examples of the chelating agents include citramalic acid, agaric acid, glyceric acid, shikimic acid, hinokitiol, gallic acid, tannic acid, caffeic acid, ethylenediaminetetraacetic acid, ethyleneglycol tetraacetic acid, diethylenetriaminepentaacetic acid, phytic acid, polyphosphoric acid, and methaphosphoric acid, as well as the analogs, alkali metal salts, carboxylic esters thereof.

Examples of the ultraviolet absorbents include benzoic acid type ultraviolet absorbents such as para-aminobenzoic acid; anthranyl acid type ultraviolet absorbents such as methyl anthranilate; salicylic acid type ultraviolet absorbents such as octyl salicylate; cinnamic acid type ultraviolet absorbents such as isopropyl para-methoxycinnamate and octyl para-methoxycinnamate; urocanic acid type ultraviolet absorbents such as urocanic acid and ethyl urocanate; benzophenone type ultraviolet absorbents such as 2-hydroxy-4-methoxybenzophenone and dihydroxybenzophenone; benzotriazole type ultraviolet absorbents, and 2-phenylbenzimidazole-5-sulfonic acid.

Examples of the humectants include polyethylene glycol (hereafter referred to as PEG), propylene glycol, dipropylene glycol, 1,3-butylene glycol, glycerin, diglycerin, xylitol, maltitol, maltose, D-mannitol, glucose, fructose, sodium chondroitin sulfate, sodium hyaluronate, sodium lactate, glucosamine, and cyclodextrin.

Examples of the medicinal ingredients to be blended in include vitamins such as vitamin A oil, retinol, retinol palmitate, pyridoxine chloride, benzyl nicotinate, nicotinic acid amide, dl-α-tocopherol nicotinate, magnesium ascorbate phosphate, vitamin $D_2$, dl-α-tocopherol, pantothenic acid, and biotin; anti-inflammatory agents such as azulene and glycyrrhizin; whitening agents such as arbutin, 4-methoxysalicilic acid, tranexamic acid, ethyl vitamin C, and magnesium ascorbate phosphate; hormones such as estradiol; astringents such as zinc oxide and tannic acid; tonics such as L-menthol and camphor; as well as lysozyme chloride, pyridoxine hydrochloride, and sulfur. Furthermore, various extracts manifesting various medicinal effects can be blended in. Examples include *houttuynia cordata* extract, Phellodendri Cortex extract, licorice extract, peony extract, moutan cortex extract, loofah extract, saxifrage extract, eucalyptus extract, clove extract, horse chestnut extract, corn flower extract, sea weed extract, and thyme extract.

Examples of the preservatives include benzoic acid, salicylic acid, para-hydroxybenzoate (such as methylparaben, ethylparaben, and butylparaben), sorbic acid, parachlorometacresol, hexachlorophene, benzalkonium chloride, chlorhexidine chloride, trichlorocarbanilide, photosensitive substances, and phenoxyethanol.

Examples of other optional ingredients that can be blended into the preparation of the present invention include neutralizers such as 2-amino-2-methyl-1-propanol, 2-amino-2-methyl-1,3-propanediol, potassium hydroxide, potassium hydroxide, triethanolamine, and sodium carboxylate; pH adjustment agents such as lactic acid, citric acid, glycolic acid, succinic acid, tartaric acid, maleic acid, sodium hydrogen carbonate, and ammonium hydrogen carbonate; and antioxidants such as ascorbic acid, α-tocopherol, and carotenoid.

EXAMPLES

The present invention is described in detail below by referring to specific examples. The present invention is not limited to these examples. The blend ratios in Examples are in wt % units.

Formulations shown in Table 1 or Table 2 were used to prepare oil-in-water emulsified skin cosmetics (cream) and the following evaluation test was conducted with a panel of ten women.

"Long-Term Moisture-Retention Effect Evaluated by Instrumental Analysis"

The moisture-retention effect was measured by instrumental analysis for the product samples (cream) of the oil-in-water emulsified skin cosmetic shown in Table 1.

Figure 2:
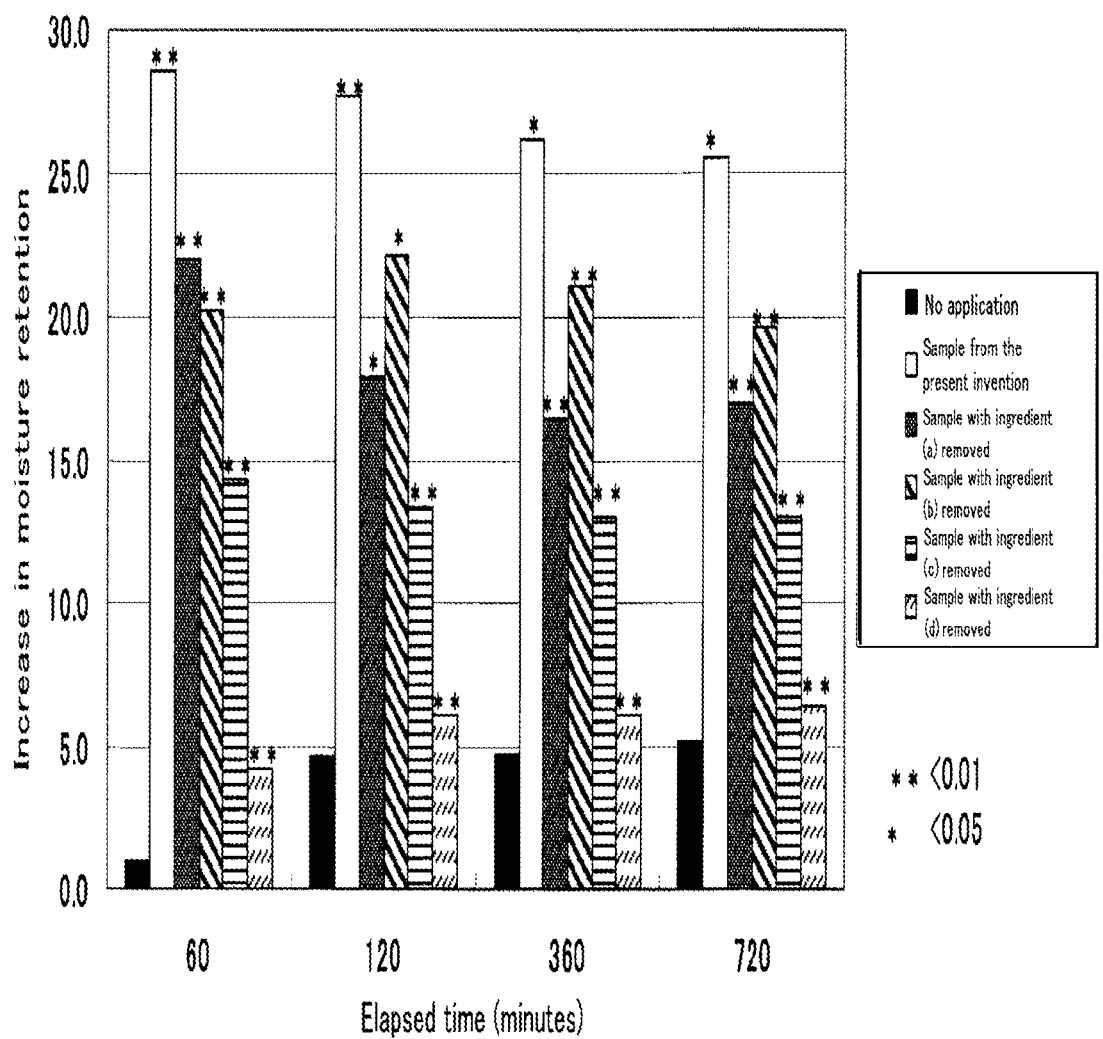
FIG. 2 is an illustration that shows the result of the moisture-retention effect based on the instrumental analysis.

For the moisture-retention effect measurement, a moisture meter Corneometer CM825 from Integral Corporation was used; the inside forearm as shown in FIG. 1 was used as the measurement site and 9 μl was applied on 9 cm² per sample. A total of six samples, i.e., including one site with no application, one of Example 1 of the present invention, one with ingredient (A) removed, one with ingredient (B) removed, one with ingredient (C) removed, and one with ingredient (D) removed, were applied on sites L1-L3 and R1-R3 on the forearm shown in FIG. 1. The increase in moisture retention (moisture level) was measured 60 minutes, 120 minutes, 360 minutes, and 720 minutes after the application. FIG. 2 shows the increase in the moisture retention of each sample.

The results in FIG. 2 indicate that the oil-in-water emulsified skin cosmetic of the present invention is excellent in terms of the long-term moisture-retention effect.

Therefore, the results of the instrumental analysis also indicate that the oil-in-water emulsified skin cosmetic of the present invention manifests a superior effect on the sustention of the emollient sensation in particular.

"Evaluation of the Usability"

Furthermore, the oil-in-water emulsified skin cosmetics (cream) of Table 1 and Table 2 were evaluated using the following methods for spreadability in the skin, absorption into the skin, absence of stickiness, the emollient sensation right after the application, the emollient sensation 12 hours after the application, the taut sensation right after the application, the taut sensation after one month of continuous use, the improvement effect on wrinkles/sagging right after the application, and the improvement effect on wrinkles/sagging after one month of continuous use. The evaluation results are shown in Table 1 and Table 2.

"Spreadability on the Skin"

Spreadability on the skin was evaluated with actual use testing by a panel of ten female specialists based on the following evaluation criteria.
(Evaluation Criteria)
◎: All 10 of them judged that spreading was light and smooth.
○: 7-9 of them judged that spreading was light and smooth.
Δ: 3-6 of them judged that spreading was light and smooth.
x: 0-2 of them judged that spreading was light and smooth.

"Absorption into the Skin"

Absorption into the skin was evaluated with actual use testing by a panel of ten female specialists based on the following evaluation criteria.
(Evaluation Criteria)
◎: All 10 of them judged that absorption into the skin occurred.
○: 7-9 of them judged that absorption into the skin occurred.
Δ: 3-6 of them judged that absorption into the skin occurred.
x: 0-2 of them judged that absorption into the skin occurred.

"Stickiness"

Stickiness was evaluated with actual use testing by a panel of ten female specialists based on the following evaluation criteria.
(Evaluation Criteria)
◎: All 10 of them judged that there was no stickiness and there was a moist sensation.
○: 7-9 of them judged that there was no stickiness and there was a moist sensation.
Δ: 3-6 of them judged that there was no stickiness and there was a moist sensation.
x: 0-2 of them judged that there was no stickiness and there was a moist sensation.

"Emollient Sensation Right after the Application and 12 Hours after Application"

The emollient sensation right after the application and 12 hours after the application was evaluated with actual use testing by a panel of ten female specialists based on the following evaluation criteria.
(Evaluation Criteria)
◎: All 10 of them judged that there was an emollient sensation.
○: 7-9 of them judged that there was an emollient sensation.
Δ: 3-6 of them judged that there was an emollient sensation.
x: 0-2 of them judged that there was an emollient sensation.

"Taut Sensation Right after the Application and after One Month of Continuous Use"

The taut sensation right after the application and one month after continuous use was evaluated with actual use testing by a panel of ten female specialists based on the following evaluation criteria.
(Evaluation Criteria)
◎: All 10 of them judged that there was a taut sensation.
○: 7-9 of them judged that there was a taut sensation.
Δ: 3-6 of them judged that there was a taut sensation.
x: 0-2 of them judged that there was a taut sensation.

"Wrinkles/Sagging Improvement Effect Right after the Application and after One Month of Continuous Use"

The wrinkles/sagging improvement effect right after the application and one month after continuous use was evaluated with actual use testing by a panel of ten female specialists based on the following evaluation criteria.
(Evaluation Criteria)
◎: All 10 of them judged that there was a wrinkles/sagging improvement effect.
○: 7-9 of them judged that there was a wrinkles/sagging improvement effect.
Δ: 3-6 of them judged that there was a wrinkles/sagging improvement effect.
x: 0-2 of them judged that there was a wrinkles/sagging improvement effect.

(Test Formulations)

TABLE 1

| Ingredient name | Sample of the present invention Example 1 | Ingredient (A) removed | Ingredient (B) removed | Ingredient (C) removed | Ingredient (D) removed | Ingredient (E) removed | Ingredient (G) oil component less than 25 wt % |
|---|---|---|---|---|---|---|---|
| (1) Ion-exchanged water | Balance | Balance | Balance | Balance | Balance | Balance | Balance |
| (2) 1,3-butylene glycol | 6.0 | 6.0 | 6.0 | 6.0 | 6.0 | 6.0 | 6.0 |
| (3) Phenoxyethanol | 0.5 | 0.5 | 0.5 | 0.5 | 0.5 | 0.5 | 0.5 |
| (4) Ingredient (A) Acetylated hyaluronic acid *1) | 0.005 | — | 0.005 | 0.005 | 0.005 | 0.005 | 0.005 |

TABLE 1-continued

| Ingredient name | Sample of the present invention Example 1 | Ingredient (A) removed | Ingredient (B) removed | Ingredient (C) removed | Ingredient (D) removed | Ingredient (E) removed | Ingredient (G) oil component less than 25 wt % |
|---|---|---|---|---|---|---|---|
| (5) Polyoxyethylene (20) behenyl ether | 0.7 | 0.7 | 0.7 | 0.7 | 0.7 | 0.7 | 0.7 |
| (6) Ingredient (G) oil component petrolatum | 2.0 | 20 | 2.0 | 2.0 | 2.0 | 2.0 | 1 |
| (7) Ingredient (G) oil component palm hydrogenated oil | 1.5 | 1.5 | 1.5 | 1.5 | 1.5 | 1.5 | 0.75 |
| (8) Ingredient (G) oil component myristyl myristate | 0.5 | 0.5 | 0.5 | 0.5 | 0.5 | 0.5 | 0.5 |
| (9) Ingredient (G) oil component Behenyl alcohol | 3.3 | 3.3 | 3.3 | 3.3 | 3.3 | 3.3 | 3.3 |
| (10) Ingredient (G) oil component Stearyl alcohol | 0.9 | 0.9 | 0.9 | 0.9 | 0.9 | 0.9 | 0.9 |
| (11) Ingredient (G) oil component Trioctanoin | 15.0 | 15.0 | 15.0 | 15.0 | 15.0 | 15.0 | 10.0 |
| (12) Ingredient (G) oil component Isodecyl pivalate | 2.0 | 2.0 | 2.0 | 2.0 | 2.0 | 2.0 | 1 |
| (13) Ingredient (G) oil component Dimethicone (6 mPa·s) | 3.0 | 3.0 | 3.0 | 3.0 | 3.0 | 3.0 | 1.5 |
| (14) Ingredient (C) mixture of dimethicone crosspolymer/dimethicone *2) | 8.0 (Net 1.28) | 8.0 (Net 1.28) | 8.0 (Net 1.28) | — | 8.0 (Net 1.28) | 8.0 (Net 1.28) | 8.0 (Net 1.28) |
| (15) Ingredient (E) Polyvinyl alcohol | 0.3 | 0.3 | 0.3 | 0.3 | 0.3 | — | 0.3 |
| (16) Ingredient (D) Glycerin | 7.0 | 7.0 | 7.0 | 7.0 | — | 7.0 | 7.0 |
| (17) Dipropylene glycol | 3.0 | 3.0 | 3.0 | 3.0 | 3.0 | 3.0 | 3.0 |
| (18) Ingredient (F) Sodium N,N'-dimethylacrylamide-2-acrylamide-2-methlylpropane sulfonate/N,N'-methylenebisacrylamide copolymer *3) | 0.3 | 0.3 | 0.3 | 0.3 | 0.3 | 0.3 | 0.3 |
| (19) Ingredient (B) Polymethacryloyloxyethyl phosphorylcholine derivative *4) | 2.0 (Net 0.1) | 2.0 (Net 0.1) | — | 2.0 (Net 0.1) | 2.0 (Net 0.1) | 2.0 (Net 0.1) | 2.0 (Net 0.1) |
| Spreadability on the skin | ⊚ | Δ | Δ | ○ | ⊚ | ⊚ | ⊚ |
| Absorption into the skin | ⊚ | ○ | Δ | ○ | ○ | ⊚ | ○ |
| Absence of the sticky sensation | ⊚ | ○ | X | X | ⊚ | ⊚ | ⊚ |
| Emollient sensation right after application | ⊚ | ○ | ○ | ○ | X | ○ | Δ |
| Emollient sensation 12 hours after application | ⊚ | Δ | ○ | Δ | X | ○ | Δ |
| Taut sensation right after application | ⊚ | Δ | Δ | X | Δ | X | Δ |
| Taut sensation after one month of continuous use | ⊚ | Δ | Δ | ○ | Δ | X | Δ |
| Wrinkles/sagging improvement effect right after application | ⊚ | Δ | Δ | X | X | X | Δ |
| Wrinkles/sagging improvement effect after one month of continuous use | ⊚ | ○ | Δ | ○ | X | X | Δ |

*1: Acetylated hyaluronic acid having a limiting viscosity of 100 cm$^3$/g and an acetyl group substitution number of 3.2
*2: Product name: 9041 Silicone Elastomer Blend from Dow Corning Toray Company Ltd. (Swollen form having a non-emulsifying cross-linked silicone content of 16%, solvent dimethicone 5 mPa·s)
*3: Sodium N,N'-dimethylacrylamide-2-acrylamide-2-methlylpropane sulfonate/N,N'-methylenebisacrylamide copolymer Product name SU Polymer G1 from TOHO Chemical Industry
*4: Product name: LIPIDURE-PMB (molecular weight 600,000, x/y = 8/2) from NOF Corporation, blend ratio of ingredient (B) of the present invention: 5 wt %

Next, the effect of the present invention is demonstrated by referring to Examples and Comparative examples.
(Test Formulations)

TABLE 2

| Ingredient name | Example 2 | Example 3 | Example 4 | Comparative example 1 | Comparative example 2 | Comparative example 3 | Comparative example 4 |
|---|---|---|---|---|---|---|---|
| (1) Ion-exchanged water | Balance | Balance | Balance | Balance | Balance | Balance | Balance |
| (2) 1,3-butylene glycol | 6.0 | 6.0 | 6.0 | 6.0 | 6.0 | 6.0 | 6.0 |
| (3) Phenoxyethanol | 0.5 | 0.5 | 0.5 | 0.5 | 0.5 | 0.5 | 0.5 |
| (4) Ingredient (A) Acetylated hyaluronic acid *5) | 0.001 | 0.05 | 0.1 | 0.05 | — | 0.1 | 0.05 |
| (5) Control for ingredient (A) Hyaluronic acid *6) | — | — | — | — | 0.1 | — | — |
| (6) Self-emulsifying glycerin monostearate | 2.0 | 2.0 | 2.0 | 2.0 | 2.0 | 2.0 | 2.0 |
| (7) Polyethylene glycol monostearate (polyoxyethylene 40 mole adduct) | 1.5 | 1.5 | 15 | 1.5 | 1.5 | 1.5 | 1.5 |
| (8) Sorbitan tristearate | 0.1 | 0.1 | 0.1 | 0.1 | 0.1 | 0.1 | 0.1 |
| (9) Ingredient (G) oil component Microcrystalline wax | 2.0 | 2.0 | 2.0 | 2.0 | 2.0 | 2.0 | 2.0 |
| (10) Ingredient (G) oil component Cetanol | 4.0 | 4.0 | 4.0 | 4.0 | 4.0 | 4.0 | 4.0 |
| (11) Ingredient (G) oil component Behenyl alcohol | 3.5 | 3.5 | 3.5 | 3.5 | 3.5 | 3.5 | 3.5 |
| (12) Ingredient (G) oil component Stearyl alcohol | 1.0 | 1.0 | 1.0 | 1.0 | 1.0 | 1.0 | 1.0 |
| (13) Ingredient (G) oil component Glyceryl tricaprylate | 5.0 | 5.0 | 5.0 | 5.0 | 5.0 | 5.0 | 5.0 |
| (14) Ingredient (G) oil component Isododecane | 7.0 | 7.0 | 7.0 | 7.0 | 7.0 | 7.0 | 7.0 |

TABLE 2-continued

| Ingredient name | Example 2 | Example 3 | Example 4 | Comparative example 1 | Comparative example 2 | Comparative example 3 | Comparative example 4 |
|---|---|---|---|---|---|---|---|
| (15) Ingredient (G) oil component Dimethicone (2 mPa·s) | 5.0 | 5.0 | 5.0 | 5.0 | 5.0 | 5.0 | 5.0 |
| (16) Ingredient (C) mixture of (dimethicone/vinyl dimethicone) crosspolymer/dimethicone *7) | 2.0 (Net 0.5) | 10.0 (Net 2.5) | 20.0 (Net 5.0) | — | 10.0 (Net 2.5) | — | 10.0 (Net 2.5) |
| (17) Polyvinyl alcohol | 0.3 | 0.3 | 0.3 | 0.3 | 0.3 | 0.3 | 0.3 |
| (18) Control for ingredient (C) (Alkyl acrylate/dimethicone) copolymer *8) | — | — | — | 10.0 (Net 3.0) | — | 10.0 (Net 3.0) | — |
| (19) Ingredient (D) Glycerin | 5.0 | 7.5 | 10.0 | 7.5 | 7.5 | 7.5 | 7.5 |
| (20) Dipropylene glycol | 3.0 | 3.0 | 3.0 | 3.0 | 3.0 | 3.0 | 3.0 |
| (21) Ingredient (F) Vinylpyrrolidone/2-acrylamide-2-methylpropanesulfonic acid copolymer | 0.3 | 0.3 | 0.3 | 0.3 | 0.3 | 0.3 | — |
| (22) Control for ingredient F (thickener) Xanthan gum | — | — | — | — | — | — | 0.3 |
| (23) Ingredient (B) Polymethacryloyloxyethyl phosphorylcholine derivative *10) | 0.06 (Net 0.003) | 3.0 (Net 0.15) | 6.0 (Net 0.3) | — | — | 3.0 | 3.0 (Net 0.15) |
| (24) Control for ingredient (B) Hydrogenated lecithin *11) | — | — | — | 1.0 | 1.0 | — | — |
| Spreadability on the skin | ◎ | ◎ | ◎ | Δ | ○ | Δ | Δ |
| Absorption into the skin | ◎ | ◎ | ◎ | X | Δ | ○ | Δ |
| Absence of the sticky sensation | ◎ | ◎ | ◎ | X | Δ | X | Δ |
| Emollient sensation right after application | ○ | ◎ | ◎ | ○ | ○ | ○ | ○ |
| Emollient sensation 12 hours after application | ○ | ◎ | ◎ | Δ | Δ | X | ○ |
| Taut sensation right after application | ○ | ◎ | ◎ | Δ | Δ | Δ | Δ |
| Taut sensation after one month of continuous use | ○ | ◎ | ◎ | Δ | ○ | Δ | Δ |
| Wrinkles/sagging improvement effect right after application | ○ | ○ | ◎ | Δ | Δ | X | Δ |
| Wrinkles/sagging improvement effect after one month of continuous use | ○ | ◎ | ◎ | Δ | ○ | X | Δ |

*5: Acetylated hyaluronic acid having a limiting viscosity of 160 cm$^3$/g and an acetyl group substitution number of 2.8
*6: Sodium hyaluronate having a molecular weight of 900,000
*7: Product name: KF-16 from Shin-Etsu Chemical Co., Ltd. Swollen form having a non-emulsifying cross-linked silicone content of 25%, solvent dimethicone 6 mPa·s
*8: Product name: KF-545 from Shin-Etsu Chemical Co., Ltd. Polymer content: 30%, solvent cyclopentasiloxane
*9: Product name: Aristoflex AVC from Clariant (Japan) K. K.
*10: Product name: LIPIDURE-PMB (Ph) (molecular weight 600,000, x/y = 8/2) from NOF Corporation Blend ratio of ingredient (B) of the present invention: 5%
*11: Product name: COATSOME NC-21 from NOF Corporation The results of the aforementioned Table 1 and Table 2 indicate that Examples 1-4 of the invention of the present application are superior in terms of spreadability on the skin, absence of stickiness, the emollient sensation right after application, the emollient sensation 12 hours after application, and the taut sensation.

In contrast, the samples of Table 1 that have one of (A)-(G) removed and Comparative examples 1-4 of Table 2 clearly lack some of the aforementioned effects.

More Examples pertaining to the present invention are shown below. The oil-in-water emulsified skin cosmetics of Examples 5-9 are all oil-in-water emulsified skin cosmetics that are superior in terms of the effects of the present invention.

Example 5

Whitening and Emollient Cream (O/W Type)

| Ingredients | Blend ratio (wt %) |
|---|---|
| (1) Stearyl alcohol | 2.0 |
| (2) Behenyl alcohol | 1.0 |
| (3) Hydrogenated polyisobutene | 6.0 |
| (4) Dimethicone (1.5 mPa·s) | 7.0 |
| (5) Squalane | 7.0 |
| (6) Tripropylene glycol dineopentanoate | 2.0 |
| (7) 1,3-butylene glycol | 5.0 |
| (8) Ingredient (D) Glycerin | 10.0 |
| (9) Dipropylene glycol | 3.0 |
| (10) Ingredient (A) Acetylated hyaluronic acid Limiting viscosity: 200 cm$^3$/g, acetyl group substitution number: 2.6 | 0.005 |
| (11) Ingredient (C) Mixture of dimethicone crosspolymer/dimethicone (Cross-linked silicone content: 3.0%) Product name: 9045 Silicone Elastomer Blend [Non-emulsifying cross-linked silicone content 12%] from Dow Corning Toray Company Ltd. | 25.0 |
| (12) Ingredient (B) Polymethacryloyloxyethyl phosphorylcholine derivative [Ingredient (B) content 0.05%] Product name: LIPIDURF-PMB (BG) [Ingredient (B) content 5%] from NOF Corporation | 0.1 |
| (13) Polyethylene glycol 1500 | 1.0 |
| (14) Polyoxyethylene (20) sorbitan monococoate Product name: NIKKOL TL-10V from Nikko Chemicals Co., Ltd. | 3.0 |
| (15) Glyceryl monostearate | 2.0 |
| (16) Ethylparaben | 0.1 |
| (17) Butylparaben | 0.1 |

-continued

| Ingredients | Blend ratio (wt %) |
|---|---|
| (18) Tocopherol | 0.1 |
| (19) Ascorbic acid glucoside | 2.0 |
| (20) Perfume | Appropriate amount |
| (21) Ion-exchanged water | Balance |
| (22) Sodium hydroxide | Appropriate amount |
| (23) Ingredient (F) Vinyl pyrrolidone/2-acrylamide-2-methylpropanesulfonic acid copolymer Product name: ARISTOFLEX AVS from Clariant (Japan) K.K. | 0.5 |
| (24) Ingredient (E) Polyvinyl alcohol | 0.8 |

<Preparation Method>

(7), (8), (9), (10), (12), (13), (16)-(19), (22), (23), and (24) were added to (21) and the temperature was raised to 70° C. for swelling. Next, the oil phase consisting of (1)-(6), (11), (14), (15), and (20) were prepared and the temperature was adjusted to 70° C. This was added to the aforementioned water phase and the emulsified particles were homogenized with a homomixer, followed by deaeration, cooling, and filtration to obtain the target whitening and emollient cream (O/W type).

Example 6

Emulsion

| Ingredients | Blend ratio (wt %) |
|---|---|
| (1) Dimethicone (5 mPa · s) | 10.0 |
| (2) Ingredient (C) Mixture of polysilicone-11/decamethylcyclopentasiloxane [Ingredient (C) content 0.6%] Product name: GRANSIL GCM-5 [Non-emulsifying cross-linked silicone content 6%] from Grant Industries | 10.0 |
| (3) Squalane | 5.0 |
| (4) Olefin oligomer | 6.0 |
| (5) Isotridecyl isononanoate | 5.0 |
| (6) PEG (20) stearate Product name: EMALEX 820 from Nihon Emulsion Co., Ltd. | 0.3 |
| (7) Sorbitan sesquistearate Product name: NIKKOL SS-15V from Nikko Chemicals | 0.1 |
| (8) Glyceryl monostearate (self emulsifying) Product name: NIKKOL MGS-ASEV from Nikko Chemicals | 0.3 |
| (9) Perfume | Appropriate amount |
| (10) Dipropylene glycol | 1.0 |
| (11) 1,3-butylene glycol | 4.0 |
| (12) Ingredient (D) glycerin | 6.0 |
| (13) Carboxyvinyl polymer | 0.1 |
| (14) Alkyl-modified carboxyvinyl polymer | 0.05 |
| (15) Potassium hydroxide | Appropriate amount |
| (16) Ingredient (A) Acetylated hyaluronic acid Limiting viscosity: 120 cm³/g, acetyl group substitution number: 3.0 | 0.01 |
| (17) Ingredient (B) Polymethacryloyloxyethyl phosphorylcholine derivative [Ingredient (B) content 0.005%] Product name: LIPIDURE-PMB (Ph) [Ingredient (B) content 5%] from NOF Corporation | 0.1 |
| (18) Horsetail extract | 0.1 |
| (19) Witch hazel extract | 0.1 |
| (20) Ethanol | 5.0 |
| (21) Phenoxyethanol | 0.3 |

-continued

| Ingredients | Blend ratio (wt %) |
|---|---|
| (22) Ion-exchanged water | Balance |
| (23) Ingredient (E) Polyvinyl alcohol | 0.6 |
| (24) Ingredient (F) (Ammonium acryloyldimethyltaurate/vinyl pyrrolidone)copolymer | 0.5 |

<Preparation Method>

(10)-(24) were homogeneously dissolved at 60° C. (water phase). Next, (1) and (3)-(9) were homogeneously dissolved at 60° C., which were added to the aforementioned water phase and emulsified with a homomixer at 60° C. (2) was added to this emulsion and dispersed homogeneously with a disper. After deaeration, cooling, and filtration, the target emulsion was obtained.

Example 7

Emollient Cream (O/W Type)

| Ingredients | Blend ratio (wt %) |
|---|---|
| (1) Behenyl alcohol | 0.1 |
| (2) Batyl alcohol | 0.5 |
| (3) Hydrogenated polyisobutene | 5.0 |
| (4) Liquid paraffin | 5.0 |
| (5) Cetyl ethylhexanoate | 6.0 |
| (6) Decamethylcyclopentasiloxane | 10.0 |
| (7) Ingredient (C) Mixture of (dimethicone/phenyl vinyl dimethicone) crosspolymer/diphenylsiloxy phenyl trimethicone (Non-emulsifying cross-linked silicone 2.25%) Product name: KSG-18A [Non-emulsifying cross-linked silicone content 15%] from Shin-Etsu Chemical Co., Ltd. | 15.0 |
| (8) Perfume | Appropriate amount |
| (9) Ingredient (A) Acetylated hyaluronic acid Limiting viscosity: 90 cm³/g, acetyl group substitution number: 3.4 | 0.1 |
| (10) Polyethylene glycol 20000 | 1.0 |
| (11) Ethylparaben | 0.1 |
| (12) Butylparaben | 0.1 |
| (13) Tocopherol | 0.1 |
| (14) Ingredient (F) (Dimethylacrylamide/2-acrylamide-2-methylpropanesulfonic acid copolymer Product name: SU-Polymer G-1 from Toho Chemical Industry Co., Ltd. | 0.2 |
| (15) Ingredient (B) Polymethacryloyloxyethyl phosphorylcholine derivative [Ingredient (B) content 0.1%] Product name: LIPIDURE-PMB (Ph) [Ingredient (B) content 5%] from NOF Corporation | 2.0 |
| (16) Hawthorn extract | 0.1 |
| (17) Rose apple leaf extract | 0.1 |
| (18) *Aloe* extract | 0.1 |
| (19) Burnet extract | 0.1 |
| (20) Clove extract | 0.1 |
| (21) Herba extract | 0.1 |
| (22) Althea root extract | 0.1 |
| (23) *Lithospermum* root extract | 0.1 |
| (24) 1,3-butylene glycol | 3.0 |
| (25) Ingredient (D) glycerin | 6.0 |
| (26) Ion-exchanged water | Balance |
| (27) Potassium hydroxide | Appropriate amount |
| (28) Ingredient (E) polyvinyl alcohol | 0.8 |

<Preparation Method>

(9)-(24), (26), and (28) were added to (25) and the temperature was raised and adjusted to 70° C. Next, the oil phase consisting of (1)-(6) and (8) was prepared and the temperature was adjusted to 70° C. This was added to the water phase and the emulsified particles were homogenized with a homomixer. To this (7) was added and dispersed homogeneously with a disper. After deaeration, cooling, and filtration, the target emollient cream (O/W type) was obtained.

Example 8

Whitening and Emollient Cream (O/W Type)

| Ingredients | Blend ratio (wt %) |
| --- | --- |
| (1) Palmitic acid | 2.0 |
| (2) Cetyl alcohol | 1.5 |
| (3) Petrolatum | 4.0 |
| (4) Squalane | 13.0 |
| (5) Triethylhexanoin | 8.0 |
| (6) Sorbitan oleate<br>Product name: EMALEX SP0-100<br>from Nihon Emulsion Co., Ltd. | 2.0 |
| (7) Perfume | 0.1 |
| (8) Ingredient (C)<br>Mixture of (vinyl dimethicone/lauryl dimethicone) crosspolymer/isododecane<br>[Ingredient (C) content 2.5%]<br>Product name: KSG-42 [Non-emulsifying cross-linked silicone content 25%]<br>from Shin-Etsu Chemical Co., Ltd. | 10.0 |
| (9) Tranexamic acid | 1.0 |
| (10) Ingredient (F)<br>(Ammonium acryloyldimethyltaurate/vinyl pyrrolidone) copolymer | 0.4 |
| (11) Methylparaben | 0.1 |
| (12) Phenoxyethanol | 0.1 |
| (13) Ingredient (A) Acetylated hyaluronic acid<br>Limiting viscosity: 110 cm$^3$/g,<br>acetyl group substitution number: 3.1 | 0.08 |
| (14) Ingredient (B)<br>Polymethacryloyloxyethyl phosphorylcholine derivative [Ingredient (B) content 0.3%]<br>Product name: LIPIDURE-PMB (Ph)<br>[Ingredient (B) content 5%]<br>from NOF Corporation | 6.0 |
| (15) Ingredient (D) glycerin | 8.0 |
| (16) *Hypericum* extract | 0.1 |
| (17) Melilot extract | 0.1 |
| (18) Ion-exchanged water | Balance |
| (19) Ingredient (E) polyvinyl alcohol | 0.4 |

<Preparation Method>

(9)-(17) and (19) were added to (18) and the temperature was raised and adjusted to 70° C. Next, the oil phase consisting of (1)-(7) was prepared and the temperature was adjusted to 70° C. This oil phase was added to the water phase prepared previously, the emulsified particles were homogenized with a homomixer, and (8) was added and dispersed homogeneously with a disper. After deaeration, cooling, and filtration, the target whitening & emollient cream (O/W type) having anti-aging and whitening effects was obtained.

Example 9

Gel Essence

| Ingredients | Blend ratio (wt %) |
| --- | --- |
| (1) Ingredient (F)<br>Sodium polyacrylate/2-acrylamide-2-methylpropanesulfonic acid copolymer<br>Product name: SIMULGEL EG from SEPIC | 2.0 |
| (2) Ingredient (C)<br>Mixture of (dimethicone/vinyl dimethicone) crosspolymer/dimethicone<br>[Ingredient (C) content 0.75%]<br>Product name: KSG-16 [Non-emulsifying cross-linked silicone content 25%]<br>from Shin-Etsu Chemical Co., Ltd. | 3.0 |
| (3) Dimethicone 5 mPa · s | 20.0 |
| (4) Isodecyl pivalate | 5.0 |
| (5) Polyoxyethylene (20) behenyl ether<br>Product name: NIKKOL BB-20<br>from Nikko Chemicals | 0.5 |
| (6) Ethanol | 5.0 |
| (7) Phenoxyethanol | 0.1 |
| (8) Perfume | 0.1 |
| (9) Ion-exchanged water | Balance |
| (10) Ingredient (D) glycerin | 5.0 |
| (11) 1,3-butylene glycol | 3.0 |
| (12) Ingredient (A) Acetylated hyaluronic acid<br>Limiting viscosity: 170 cm$^3$/g,<br>acetyl group substitution number: 3.0 | 0.07 |
| (13) White lotus extract | 0.1 |
| (14) Angelica root extract | 0.1 |
| (15) Ginger extract | 0.1 |
| (16) Peony extract | 0.1 |
| (17) Ingredient (B)<br>Polymethacryloyloxyethyl phosphorylcholine derivative [Ingredient (B) content 0.25%]<br>Product name: LIPIDURE-PMB (Ph)<br>[Ingredient (B) content 5%]<br>from NOF Corporation | 5.0 |
| (18) Potassium hydroxide | Appropriate amount |
| (19) Ingredient (E) polyvinyl alcohol | 0.2 |

<Preparation Method>

(1) and (5)-(19) were homogeneously dissolved in the water phase, to which a mixture of (2)-(5) was added and dispersed homogeneously with a disper. After deaeration, cooling, and filtration, the target gel essence was obtained.

INDUSTRIAL APPLICABILITY

The present invention can provide an oil-in-water emulsified skin cosmetic manifesting superior effects in improving spreadability on the skin, absorption in the skin, absence of stickiness, emollient sensations, taut sensations, and wrinkles/sagging.

The invention claimed is:

1. An oil-in-water emulsified skin cosmetic comprising the following ingredients (A) through (G):

(A) acetylated hyaluronic acid represented by the following structural formula (I)

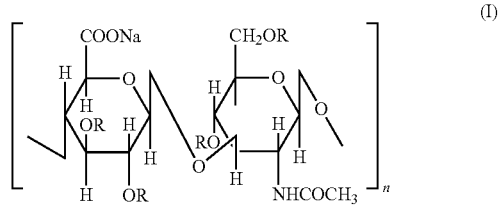

wherein R denotes H or COCH₃, and n is a real number representing the degree of polymerization;

(B) a polymethacryloyloxyethyl phosphorylcholine derivative having the following structural formula (II)

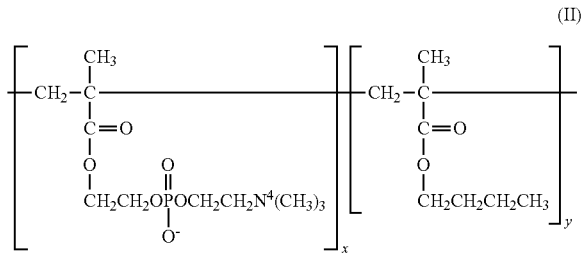

(II)

wherein x and y are real numbers representing the degrees of polymerization of the corresponding structural units, and x/y=2/8 to 8/2;

(C) one, two or more types of non-emulsifying cross-linked silicone;
(D) glycerin;
(E) polyvinyl alcohol;
(F) acrylamide-type thickener; and
(G) oil component in a total amount of 25 wt % or more relative to the total amount of the oil-in-water emulsified skin cosmetic;

wherein:
in the ingredient (A), acetylated hyaluronic acid, on average 2.6-3.8 of the four R groups are acetyl groups, and the limiting viscosity of the acetylated hyaluronic acid is 50-200 cm³/g;
the ingredient (C), one, two or more types of non-emulsifying cross-linked silicone, contains dimethicone crosspolymer or (dimethicone/vinyl dimethicone) crosspolymer or both;
the ingredient (F), acrylamide-type thickener, is vinylpyrrolidone/2-acrylamide-2-methylpropane sulfonic acid copolymer and/or sodium N,N'-dimethylacrylamide-2-acrylamide-2-methylpropane sulfonate/N,N'-methylenebisacrylamide copolymer; and
the ingredient (G), oil component, contains trioctanoin.

2. The oil-in-water emulsified skin cosmetic of claim 1 wherein
the blend ratio of said ingredient (A), acetylated hyaluronic acid, is 0.001-0.1 wt %,
the blend ratio of said ingredient (B), polymethacryloyloxyethyl phosphorylcholine derivative, is 0.003-0.3 wt %,
the blend ratio of said ingredient (C), one, two or more types of non-emulsifying cross-linked silicone, is 0.5-5.0 wt %,
the blend ratio of said ingredient (D), glycerin, is 5.0-10.0 wt %,
the blend ratio of said ingredient (E), polyvinyl alcohol, is 0.1-1.0 wt %,
the blend ratio of said ingredient (F), acrylamide type thickener, is 0.1-1.0 wt %, and
the blend ratio of said ingredient (G), oil component, is 25-40 wt %,
and the blend ratios are relative to the total amount of the oil-in-water emulsified skin cosmetic.

3. The oil-in-water emulsified skin cosmetic of claim 1 wherein the weight-average molecular weight of said ingredient (B), polymethacryloyloxyethyl phosphorylcholine derivative, is 100,000 to 1,000,000.

4. The oil-in-water emulsified skin cosmetic of claim 1 wherein said ingredient (C), one, two or more types of non-emulsifying cross-linked silicone, further contains one, two or more selected from the group consisting of (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and (dimethicone/bis-isobutyl PPG-20) crosspolymer.

5. The oil-in-water emulsified skin cosmetic of claim 2 wherein the weight-average molecular weight of said ingredient (B), polymethacryloyloxyethyl phosphorylcholine derivative, is 100,000 to 1,000,000.

6. The oil-in-water emulsified skin cosmetic of claim 2 wherein said ingredient (C), one, two or more types of non-emulsifying cross-linked silicone, further contains one, two or more selected from the group consisting of (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and (dimethicone/bis-isobutyl PPG-20) crosspolymer.

7. The oil-in-water emulsified skin cosmetic of claim 3 wherein said ingredient (C), one, two or more types of non-emulsifying cross-linked silicone, further contains one, two or more selected from the group consisting of (dimethicone/phenyl vinyl dimethicone) crosspolymer, (vinyl dimethicone/lauryl dimethicone) crosspolymer, (lauryl polydimethylsiloxyethyl dimethicone/bis-vinyl dimethicone) crosspolymer, alkyl (C30-45) cetearyl dimethicone crosspolymer, cetearyl dimethicone crosspolymer, and (dimethicone/bis-isobutyl PPG-20) crosspolymer.

* * * * *